(12) United States Patent
Auzely-Velty et al.

(10) Patent No.: US 6,858,723 B1
(45) Date of Patent: Feb. 22, 2005

(54) AMPHIPHILE CYCLODEXTRINS, PREPARATION AND USE THEREOF FOR SOLUBILIZING ORGANIZED SYSTEMS AND INCORPORATING HYDROPHOBIC MOLECULES

(75) Inventors: Rachel Auzely-Velty, Le Pont de Claix (FR); Bruno Perly, La Verriere (FR); Florence Djedaini-Pilard, Etampes (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/926,413

(22) PCT Filed: Apr. 26, 2000

(86) PCT No.: PCT/FR00/01102

§ 371 (c)(1),
(2), (4) Date: Oct. 29, 2001

(87) PCT Pub. No.: WO00/66635

PCT Pub. Date: Nov. 9, 2000

(30) Foreign Application Priority Data

Apr. 29, 1999 (FR) .............................. 99 05460

(51) Int. Cl.[7] .......................... C08B 30/18; C08B 37/16; A01N 43/04; A61K 31/715
(52) U.S. Cl. .......................... 536/46; 536/103; 536/124; 514/58; 424/1.11; 424/1.37; 424/1.65; 424/1.73
(58) Field of Search ................................. 536/103, 124, 536/46; 514/58; 424/1.73, 1.11, 1.81, 1.85, 1.37, 1.65

(56) References Cited

U.S. PATENT DOCUMENTS

| | | | |
|---|---|---|---|
| 5,821,349 A | 10/1998 | Djedaini-Pilard et al. | ... 536/103 |
| 5,993,776 A | 11/1999 | Pasqualini et al. | ......... 424/1.73 |
| 6,610,671 B2 * | 8/2003 | Buchanan et al. | ............ 514/58 |

FOREIGN PATENT DOCUMENTS

| | | |
|---|---|---|
| EP | 0 751 150 | 1/1997 |
| FR | 2 681 868 | 4/1993 |
| FR | 2 726 765 | 5/1996 |
| FR | 2 736 056 | 1/1997 |

OTHER PUBLICATIONS

Auzely–Velty, R. et al. "Micellization of Hydrophobically Modified Cyclodextrins. 1. Micellar Structure" Langmuir, 2000, 16, 3727–3734.*
Auzely–Velty, Rachel et al. "Cholesteryl–cyclodextrins: synthesis and insertion into phospholipid membranes" Carbohydrate Research, May 31, 1999, 318, 82–90.*
D. Duchene, Chapter 6, pp. 213–257, "Pharmaceutical Applications of Cyclodextrins", 1987.

A. Yabe, et al., Thin Solid Films, vol. 160, pp. 33–41, "Photoisomerization of the Azobenzenes Included in Langmuir–Blodgett Films of Cyclodextrins", 1988.

L. Jullien, et al., J. Chem. Soc. Perkin Trans. 2, pp. 1011–1020, "An Approach to Channel–Type Molecular Structures. Part 3.† Incorporation Studies of the Bouqet-Shaped $B_m$ and $B_{CD}$ in Phosphatidylcholine Vesicles‡", 1993.

A. Gulik et al., Langmuir, vol. 14, No. 5, pp. 1050–1057, "Structural Proprties of Several Amphiphile Cyclodextrins and Some Related Nanospheres. An X–Ray Scattering and Freeze–Fracture Electron Microscopy Study", 1998.

J. Lin, et al., J. Chem. Soc., Perkin Trans. 2, pp. 2639–2646, "New Amphiphilic Derivatives of Cyclodextrins for the Purpose of Insertion in Biological Membranes: The "Cup and Ball" Molecules", 1998.

K. Uekama, et al., Chem. Rev., vol. 98, No. 5, pp. 2045–2076, "Cyclodextrin Drug Carrier Systems", 1998.

(List continued on next page.)

Primary Examiner—James O. Wilson
Assistant Examiner—Traviss C. McIntosh, III
(74) Attorney, Agent, or Firm—Oblon, Spivak, McClelland, Maier & Neustadt, P.C.

(57) ABSTRACT

The invention provides cyclodextrin derivatives that may be used to transport hydrophobic molecules for pharmaceutical or cosmetic applications, by forming organised systems in an aqueous medium, alone or with phospholipids. The cyclodextrin derivatives of the present invention have the formula:

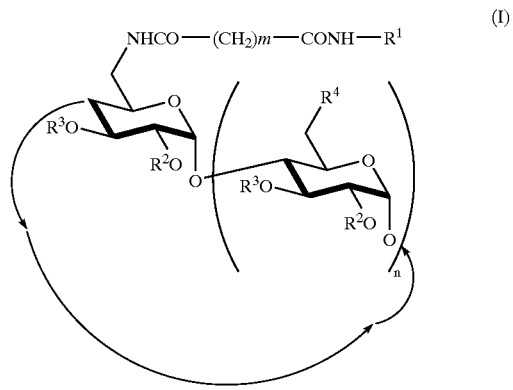

(I)

in which, $R^1$ represents a steroid, $R^2$ represents an alkyl or aryl group, substituted if applicable, $R^3$ represents H or $R^2$, all the $R^4$ represent $OR^2$, or one of the $R^4$ represents —$NHCO(CH_2)_m CONHR^1$, m is an integer ranging from 1 to 8, and n is equal to 5, 6 or 7.

18 Claims, 3 Drawing Sheets

OTHER PUBLICATIONS

F. Djedaini–Pilard, et al., Tetrahedron Letters, vol. 34, No. 15, pp. 2457–2460, "Synthesis of a New Molecular Carrier: N-(Leu–Enkephalin)yl6–Amido–6–Deoxy–Cyclomaltoheptaose", 1993.

F. Djedaini–Pilard, et al., J. Chem. Soc., Perkin Trans. 2, pp. 723–730, "Potential Formation of Intramolecular Inclusion Complexes in Peptidocyclodextrins as Evidenced by NMR Spectroscopy", 1995.

B. Lal, et al., Tetrahedron Letters, No. 23, pp. 1977–1980, "Diphenylphosphoryl Azide A Novel Reagent For The Stereospecific Synthesis of Azides from Alcohols[1] †", 1977.

R. R. C. New, IRL Press, pp. 33–48, "Preparation of Liposomes", 1990.

* cited by examiner

AMPHIPHILE CYCLODEXTRINS, PREPARATION AND USE THEREOF FOR SOLUBILIZING ORGANIZED SYSTEMS AND INCORPORATING HYDROPHOBIC MOLECULES

FIELD OF THE INVENTION

The present invention relates to new cyclodextrin derivatives, that can particularly be used to incorporate in aqueous media hydrophobic chemical compounds such as pharmaceutically active molecules, molecules with cosmetic applications and molecules used as contrast agents for medical imaging.

More specifically, it relates to amphiphilic cyclodextrin derivatives showing self-organisation properties in aqueous media and liable to be incorporated in organised surfactant systems resulting in the formation of combined systems.

Said incorporation in organised surfactant systems such as small phospholipid vesicles is intended to enable the transport of hydrophobic molecules included in the cyclodextrin, for example an active ingredient, particularly by the transmembrane route, for example the transdermal route.

STATE OF THE RELATED ART

Cyclodextrins or cyclomaltooligosaccharides are natural compounds formed by the sequencing of 6, 7 or 8 glucose units bonded in α-1→4 mode. Numerous studies have shown that these compounds could form inclusion complexes with hydrophobic molecules, thus enabling their solubilisation in aqueous media. Numerous applications have been proposed to benefit from this phenomenon, particularly in the pharmaceutical field, as described by D. Duchêne, in "Pharmaceutical Applications of Cyclodextrins", published in "Cyclodextrins and their industrial uses", Editions de Santé, Paris 1987, pp. 213–257 [1]. Pharmaceutical formulations using cyclodextrins have already been introduced onto the market in Japan, Italy and, more recently, in France, for example by Pierre Fabre Medicament for Brexin® which is an inclusion complex of Piroxicam in β-cyclodextrin.

Of the cyclodextrins that may be used, β-cyclodextrin (comprising 7 glucose units) is the most suitable in terms of the size of its cavity and is the least expensive of the three. Chemical modifications of β-cyclodextrin have been described to render it amphiphilic with a view to incorporating it in organised systems.

In this way, amphiphilic cyclodextrins comprising multiple chains on the primary face have been studied. A. Yabe et al described in "Thin Solid Films", (1988), 160, pp. 33–41 [2], the derivative per(6-dodecylamino-6-deoxy)-β-cyclodextrin in order to form stable Langmuir-Blodget layers. Similarly, L. Julien et al described in J. Chem. Soc. Perkin Trans 2, 1993, pp. 1011–1022 [3], β-cyclodextrin derivatives comprising aliphatic chains located in primary and secondary positions, with a view to incorporating said cyclodextrin derivatives in phosphatidylcholine vesicles. Said derivatives are amphiphilic and can be incorporated in the vesicles, but the internal cavity of the cyclodextrin is no longer accessible due to the significant sterio size of the aliphatic chains. Consquently, said derivatives are unable to include hydrophobic molecules, particularly active ingredient molecules.

Recently, it was demonstrated by A. Gulik et al in Langmuir (1998), 14, pp. 1050–1057 [4], that so-called "skirted" cyclodextrins, comprising fatty acid chains grafted onto secondary hydroxyls could form stable nanospheres. These molecular super-assemblies appear to show very promising encapsulation and releasing properties due to the cumulative effects of the specificity of cyclodextrin size and transport, firstly, and nanoparticle organisation, secondly. However, it is necessary to note that the synthesis and particularly the purification of such cyclodextrins remain very difficult and require long purification steps resulting in low yields. It is clear that the supramolecular organisation properties are drastically linked with the chemical purity of the amphiphilic cyclodextrin derivatives.

J. Line et al described in FR-A-2 736 056 [5] and in J. Chem. Soc. Perkin Trans 2, (1998), pp. 2638–2646 [6], the synthesis of cyclodextrin derivatives referred to as "ball joints" comprising one or more aliphatic chains giving them amphiphilic properties, without inducing a self-inclusion phenomenon of the chain(s) in the cyclodextrin. For this reason, it is possible to obtain from such derivatives inclusion complexes containing a hydrophobic molecule and the incorporation of said complexes in phospholipid vesicles. However, these molecules have proved to be relatively unstable in physiological media, i.e. at pH values greater than or equal to 7, and their incorporation abilities in organised systems remain limited. In addition, said "ball joint" molecules do not organise themselves spontaneously in aqueous media to give particles of well-defined size and shape.

DESCRIPTION OF THE INVENTION

The present invention specifically relates to amphiphilic cyclodextrin derivatives, stable in physiological media, able to include hydrophobic compounds, having good incorporation abilities in organised systems and also showing self-organisation properties in aqueous media.

According to the invention, the amphiphilic cyclodextrin derivative complying with the formula:

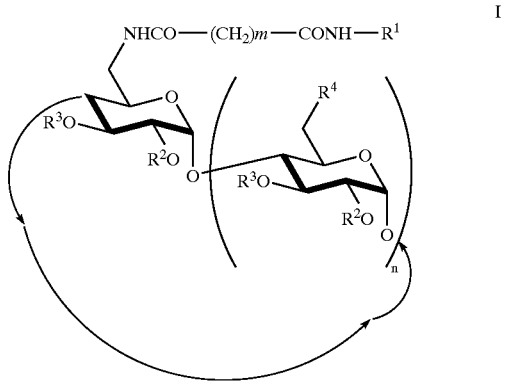

wherein:
  $R^1$ represents a group derived from a steroid,
  $R^2$ represents an alkyl or aryl group, substituted if applicable,
  $R^3$ represents H or $R^2$,
  all the $R^4$ represent $OR^2$, or
  one of the $R^4$ represents —NHCO$(CH_2)_m$CONHR$^1$, and the other $R^4$ represent $OR^2$ provided that there is at least one glucose unit where $R^4$ represents $OR^2$ between the two glucose units comprising the substituent —NHCO—$(CH_2)_m$—CONH—R$^1$,
  m is an integer ranging from 1 to 8, and
  n is equal to 5, 6 or 7.

Note that steroids are compounds derived from a polycyclic nucleus according to the formula:

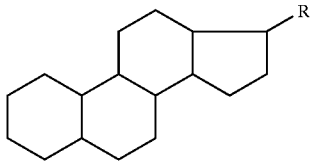

II wherein R represents a linear or ramified hydrocarbon group of 1 to 9 carbon atoms and wherein the polycyclic nucleus may comprise one or more double bonds, and one or more substituents chosen from $CH_3$, OH and O, on one or more carbon atoms of the cycles.

In the cyclodextrin derivative according to the invention, $R^1$ may represent a group derived from sterols by eliminating the hydroxyl group from the first cycle, with a degree of unsaturation of 0 to 6. It may also consist of groups derived from sterones. For example, $R^1$ may represent a group derived from cholesterol such as the group according to the formula:

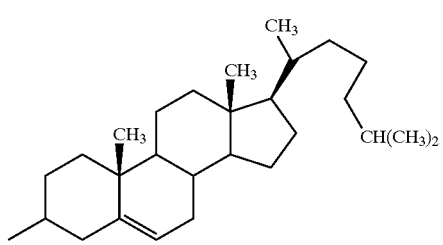

III

In the derivative according to the invention, the amphiphilic properties are obtained due to the presence of one or two substituents comprising a group derived from a steroid.

If the derivative comprises two substituents of this type, it is necessary for them not be located on two adjacent glucose units of the cyclodextrin, due to their size.

In addition, the two glucose units comprising said substituents are separated by one or two glucose units comprising an $OR^2$ substituent.

Preferentially, the cyclodextrin derivative only comprises a single substituent of this type, with all the $R^4$ representing $OR^2$.

In the cyclodextrin derivative according to the invention, the $R^2$ group represents a linear or ramified alkyl or aryl group, substituted if applicable. If an alkyl group is used, said group generally has 1 to 4 carbon atoms and is preferentially linear. The aryl group may be, for example, the phenyl group or the benzyl group. Any substituents of said alkyl or aryl groups may be, for example, halogen atoms and hydroxyl, carboxyl and amine groups. Advantageously, $R^2$ represents the methyl group.

$R^3$ may represent a hydrogen atom or an alkyl group identical or different to $R^2$. Preferentially, $R^3$ represents H.

In formula I given above, the aliphatic chain linking the steroid-derived group to the glucose unit may comprise between the two amide groups, of 1 to 8 carbon atoms. Satisfactory results are obtained with two carbon atoms, i.e. where m is equal to 2.

The cyclodextrin derivatives according to the invention may be α-, β- or γ-CD derivatives. Preferentially, β-CD derivatives are used, which corresponds in formula I given above to the case were n is equal to 6.

The cyclodextrin derivatives according to the invention may be prepared using conventional methods from the corresponding mono-azide or diazide cyclodextrin derivatives.

If it is desired to prepare a derivative according to formula I as defined above where $R^3$ represents a hydrogen atom, the method comprises the following steps:

a) react a derivative according to the formula:

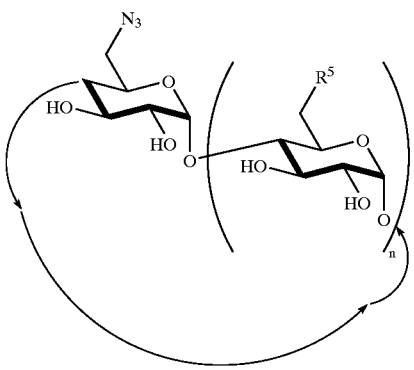

IV wherein all the $R^5$ represent OH, or one of the $R^5$ represents $-N_3$ and the other $R^5$ represent OH, provided that there is at least one glucose unit where $R^5$ represents OH between the two glucose units comprising the $N_3$ substituent, and n is equal to 5, 6 or 7, with a dialkyl sulphate $SO_4R^2_2$ where $R^2$ has the significance given above, in a basic medium to obtain the cyclodextrin derivative according to the formula:

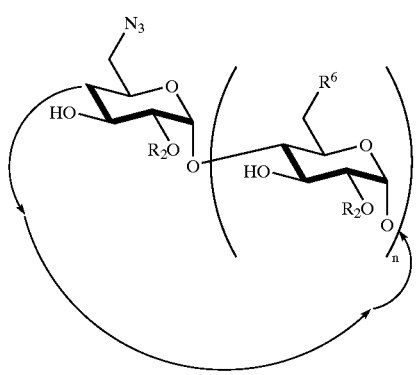

V wherein all the $R^6$ represent $OR^2$, or one of the $R^6$ represents $N_3$ and the other $R^6$ represent $OR^2$, and $R^2$ and n are as defined above, b) perform a Staudinger reaction on the derivative according to formula V using triphenylphosphine and ammonia to convert $N_3$ into $NH_2$ and obtain the derivative according to the formula;

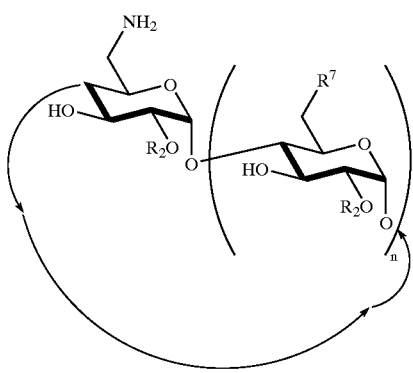

wherein all the $R^7$ represent $OR^2$, or one of the $R^7$ represents $NH_2$ and the other $R^7$ represent $OR^2$, and $R^2$ and n are as defined above, c) react the derivative according to formula VI with an acid anhydride according to the formula:

where m is as defined above, to obtain the derivative according to the formula:

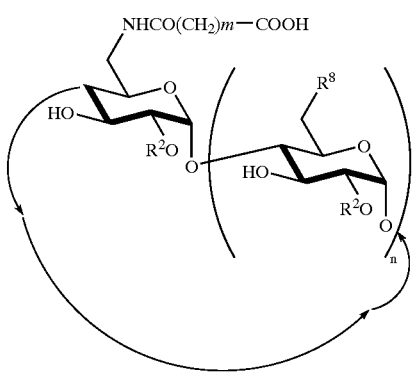

wherein all the $R^8$ represent $OR^2$, or one of the $R^8$ represents —NHCO—$(CH_2)_m$—COOH and the other $R^8$ represent $OR^2$, and $R^2$, m and n are as defined above, and d) react the derivative according to formula VIII with a compound according to the formula $NH_2$—$R^1$ to obtain the cyclodextrin derivative according to formula I defined above.

The monoazide or diazide derivatives used as the starting product in the method may be obtained from the corresponding monotosylate or ditosylate cyclodextrin derivative through the action of lithium nitride in water.

In step a of the method described above, the cyclodextrin derivative according to formula IV is reacted with a dialkyl sulphate $SO_4R^2{}_2$ in a mixture of organic solvents such as dimethylformamide DMF and dimethylsulphoxide DMSO in 50:50 proportions by volumes, in the presence of a base such as barium oxide and barium hydroxide, at 8° C. The derivative according to formula V obtained in this way may be separated using the methods described in detail in example 1.

In step b, the derivative according to formula V is reacted with trichenylphosphine in an organic solvent such as DMS and 20% ammonia is then added. The derivative according to formula VI obtained in this way may be purified by evaporating the solvent, eliminating the white precipitate formed by filtration and then separating by ion exchange chromatography. In step c, the derivative according to formula VI is reacted with the acid anhydride according to formula VII desired in an organic solvent such as DMF. The derivative according to formula VIII obtained is not isolated and the next step d is carried out directly in the same reaction medium. Peptide coupling reagents, such as N,N'-diisopropylcarbodiimide and hydroxybenzotriazole, are then added. The derivative according to formula VIII then reacts with the compound according to the formula $H_2N$—$R^1$ such as cholest-5-en-3α-ylamine. The derivative according to formula I obtained in this way may be separated from the reaction medium by evaporating the solvent and purifying by silica gel column chromatography.

If it is necessary to prepare a derivative according formula I as defined above, where $R^3$ represents $R^2$, the method comprises the same steps as above, but in step a, alkylation of all the OH groups is performed with an iodoalkane. In this case, the following steps are carried out:

a) react a derivative according to the formula:

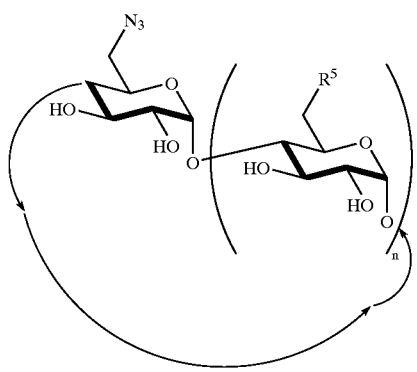

wherein all the $R^5$ represent OH, or one of the $R^5$ represents —$N_3$ and the other $R^5$ represent OH, provided that there is at least one glucose unit where $R^5$ represents OH between the two glucose units comprising the $N_3$ substituent, and n is equal to 5, 6 or 7, with an iodoalkane according to the formula $IR^2$ wherein $R^2$ has the significance given above, in the presence of NaH to obtain the cyclodextrin derivative according to the formula:

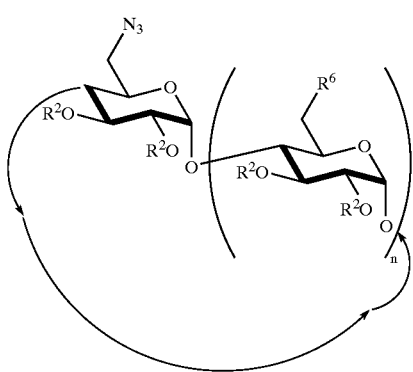

wherein all the $R^6$ represent $OR^2$, or one of the $R^6$ represents $N_3$ and the other $R^6$ represent $OR^2$, and $R^2$ and n are as defined above, b) perform a Staudinger reaction on the derivative according to formula IX using triphenylphosphine and ammonia to convert $N_3$ into $NH_2$ and obtain the derivative according to the formula:

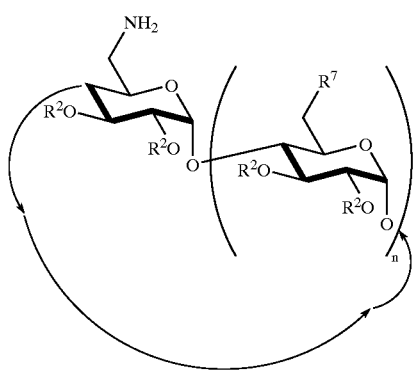

wherein all the $R^7$ represent $OR^2$, or one of the $R^7$ represents $NH_2$ and the other $R^7$ represent $OR^2$, and $R^2$ and n are as defined above, c) react the derivative according to formula X with an acid anhydride according to the formula:

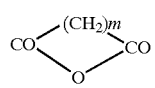

where m is as defined above, to obtain the derivative according to the formula:

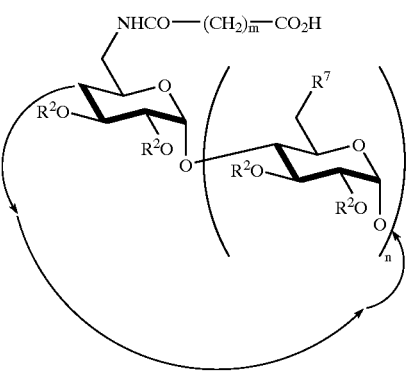

wherein all the $R^7$ represent $OR^2$ or one of the $R^7$ represents $-NHCO-(CH_2)_m-COOH$ and the other $R^7$ represent $OR^2$, and $R^2$, m and n are as defined above, and d) react the derivative according to formula XI with a compound according to the formula $NH_2-R^1$ to obtain the cyclodextrin derivative according to formula I defined above.

The invention also relates to the inclusion complexes of the cyclodextrin derivative according to formula I with a hydrophobic compound in an aqueous medium. The hydrophobic chemical compounds liable to be solubilised in aqueous media by means of said cyclodextrin derivatives I may be of different types. Examples of such compounds include cosmetic products, vitamins, pharmaceutically active molecules and molecules used as contrast agents for medical imaging, for example, the compounds described by Uekama and Irie in Chemical Review (1998), 98, pp. 2045–2076 [7].

Preferentially in the invention, the hydrophobic chemical compound is a pharmaceutically active molecule. Examples of such molecules include steroids, for example prednisolone, neurotropes such as dothiepin, bacteriostatics such as chloramphenicol, vitamins such as vitamin A, vascular wall tonics such as esculin, and contrast agents for medical imaging such as 16-iodo-3-methylhexadecanoic acid.

Said inclusion complexes may be prepared using conventional methods, for example by adding to a solution or suspension of the formula I cyclodextrin used, a solution of hydrophobic compound in a suitable organic solvent, for example acetone.

The formula I cyclodextrin derivatives are characterised in that they organise themselves spontaneously in aqueous media to give nanoparticles from 25 to 30 Å of mean radius and perfectly spherical in shape. The mean number of monomers is 24 cyclodextrin derivative molecules per nanoparticle. In addition, the invention also relates to an aqueous solution of nanoparticles of a cyclodextrin derivative according to formula I alone or in the form of an inclusion complex with a hydrophobic compound.

Said nanoparticle solution may be prepared by forming an aqueous solution of the cyclodextrin derivative or an inclusion complex of said derivative having a derivative or complex concentration greater than the critical micellar concentration of the derivative.

The self-organisation of amphiphilic cyclodextrins into nanoparticles in an aqueous medium makes it possible to transport a hydrophobic molecule, for example an active ingredient, particularly by the transmembrane or parenteral route.

Moreover, the cyclodextrin derivatives according to the invention are of particular interest since they can be incorporated into organised surfactant systems such as small phospholipid vesicles or micellae. Said incorporation is intended to enable the solubilisation of organised systems, with a view to transporting active ingredients included in the cyclodextrin derivative.

In addition, the invention also relates to an organised surfactant system comprising a cyclodextrin derivative or an inclusion complex of said derivative according to the invention. The surfactants liable to form such organised systems may be of different types. Examples include the phospholipids complying with the following general formula:

XII

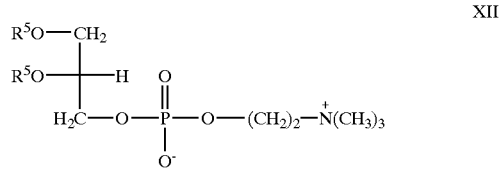

wherein $R^5$ represents $CH_3$—$(CH_2)_p$—CO where p is an integer ranging from 6 to 18. Said phospholipids are capable of forming small unilamellar vesicles. This particularly applies to dimyristoylphosphatidylcholine DMPC which complies with the above formula where p=12.

To incorporate the cyclodextrin derivative or an inclusion complex of said derivative according to the invention in the organised surfactant system, it is possible to form small DMPC vesicles beforehand by sonication and then add in the aqueous solution the cyclodextrin derivative or the inclusion complex. The combined system obtained in this way then becomes perfectly soluble in water, resulting in a clear solution. The combined system obtained in this specific case is a combined micella of a mean radius of 60 Å.

In addition, the invention also relates to an aqueous solution comprising in solution a combined system formed from phospholipid or membrane protein vesicles, and at least one cyclodextrin derivative or at least one cyclodextrin derivative inclusion complex according to the invention.

Such solutions are beneficial since they enable the transport of hydrophobic molecules, for example an active ingredient, by the transmembrane or parenteral route, for pharmaceutical or cosmetic applications.

The invention's other characteristics and advantages will be seen more clearly upon reading the following examples, which are naturally illustrative and not exhaustive, with reference to the appended FIGS. 1 to 5.

DETAILED DESCRIPTION OF EMBODIMENTS

EXAMPLE 1

Figure 1:
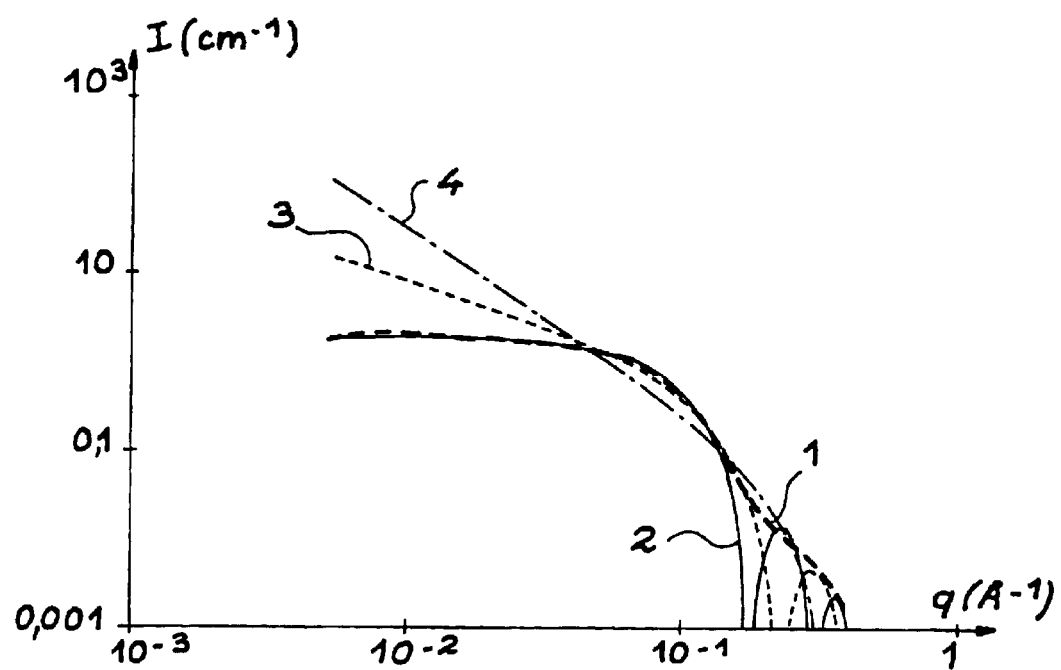
FIG. 1 illustrates the experimental neutron diffusion spectrum, on a logarithmic scale, of an aqueous solution of nanoparticles of the cyclodextrin derivative obtained in example 1 with three theoretical curves of spherical micellae, cylindrical micellae and double layers.

Synthesis of mono-6-(cholest-5-en-3α-ylaamide) succinylamide-6-deoxy-2,2',2'',2''',2'''',2''''',2'''''',6,6', 6'',6''',6'''',6''''',6''''''-trideca-O-methyl-cyclomaltoheptaose.

This compound is the derivative according to formula I where $R^1$ represents the group according to formula III, $R^2$ is the methyl group, $R^3$ represents H, all the $R^4$ represent $OCH_3$, m is equal to 2 and n is equal to 6.

a) Preparation of mono-6-azide-6-deoxy-2,2',2'',2''',2'''', 2''''',2'''''',6,6',6'',6''',6'''', 6''''',6''''''-trideca-O-methyl-cyclomaltoheptaose.

In a flask, 2 g (1.7 mmol) of mono-6-azide-6-deoxy-cyclomaltoheptaose (obtained for example according to the protocol described in Tetrahedron Lett. (1993), 34, pp. 2457–2460 [8] and J. Chem. Soc. Perkin Trans 2 (1995), pp. 723–730) [9]) is dissolved in 15 ml of anhydrous dimethylsulphoxide. This solution is supplemented with 15 ml of anhydrous dimethylformamide DMF. In a nitrogen atmosphere and under vigorous stirring, 3.8 g (~12 mmol) of barium hydroxide octohydrate and 3.6 g (~24 mmol) of barium oxide are then added. After homogenising the medium, 8 ml of dimethyl sulphate (~84 mmol) is added, and the mixture is left under vigorous stirring, in a nitrogen atmosphere, for 30 hours at 8° C. The milky suspension is then supplemented with 5 ml of 20% ammonia and stirred for 3 hours at ambient temperature. The suspension is allowed to settle overnight in a refrigerator. After concentrating the supernatant at reduced pressure, the residual solid is taken up with 100 ml of dichloromethane, and two more times with 50 ml of dichloromethane. The organic phases are pooled, washed 3 times with 20 ml of an aqueous solution saturated with sodium chloride, twice with 20 ml of m water, dried on magnesium sulphate and concentrated at reduced pressure. The product is precipitated by adding 100 ml of n-hexane, filtered, washed with 100 ml of n-hexane and dried in a vacuum.

0.80 g (0.60 mmol) of mono-6-azide-6-deoxy-2,2',2'',2''', 2'''',2''''',2'''''',6',6'',6''', 6'''', 6''''',6''''''-trideca-O-methyl-cyclomaltoheptaose, which is presented in the form of a white powder, is collected.

b) Preparation of mono-6-amino-6-deoxy-2,2',2'',2''',2'''', 2''''',2'''''',6',6'',6''', 6'''', 6''''',6''''''-trideca-O-methyl-cyclomaltoheptaose.

0.75 g (0.56 mmol) of the compound obtained in a is dissolved in 30 ml of DMF. To this solution, 0.75 g (2.86 mmol) of triphenylphosphine in 5 ml of DMF is added drop by drop, under stirring at ambient temperature. The reaction medium is maintained at ambient temperature for 2 hours, cooled to 0° C. and treated with 14 ml of 20% ammonia. It is left for 18 hours at ambient temperature under stirring, and the solvent is then eliminated at reduced pressure and the residual solid is taken up with 30 ml of water. The insoluble excess of triphenylphosphine and the corresponding oxide is eliminated by filtration. The solution is concentrated in a vacuum and the product is purified by ion exchange resin column chromatography (Lewatit® SP 1080 resin in H$^+$ form). 0.35 g (0.27 mmol) of mono-6-amino-6-deoxy-2,2', 2'',2''',2'''',2''''',2'''''', 6',6'',6''', 6'''',6''''',6''''''-trideca-O-methyl-cyclomaltoheptaose, which is presented in the form of a white powder, is collected.

c) Preparation of mono-6-(cholest-5-en-3α-ylamide)succinylamide-6-deoxy-2,2',2'',2''',2'''', 2''''',2'''''',6',6'',6''', 6'''',6''''',6''''''-trideca-O-methyl-cyclomaltoheptaose.

To a solution of 0.25 g (0.19 mmol) of the compound obtained in b in 6 ml of anhydrous DMF, 0.019 g (0.19 mmol) of succinic anhydride in 2 ml of anhydrous DMF is added in a nitrogen atmosphere under stirring. The reaction medium is maintained at ambient temperature for 5 hours, and then supplemented with 0.11 ml (0.76 mmol) of N,N'-diisopropylcarbodiimide and 0.028 g (0.19 mmol) of hydroxybenzotriazole in 2 ml of anhydrous DMF. After 30 minutes of stirring at ambient temperature, 0.089 g (0.23 mmol) of cholest-5-en-3α-ylamine (obtained in two steps from cholest-5-en-3β-ol according to the protocols described in Tetrahedron Lett. (1977), pp. 1977–1980 [10]) is added. The reaction medium is left under stirring at ambient temperature for 48 hours, hydrolysed by adding 0.30 ml of water and concentrated under reduced pressure. The residual solid is purified by silica gel column chromatography (60 Fluka silica gel; eluent: $CH_2Cl_2$—MeOH 95:5 followed by 9:1 (v/v)). 0.24 g of mono-6-(cholest-5-en-3α-ylamide)succinylamide-6-deoxy-2,2',2'',2''', 2'''',2''''',2'''''',6', 6'',6''',6'''',6''''',6''''''-trideca-O-methyl-cyclomaltoheptaose is collected.

(71% final compound yield from mono-6-amino-6-deoxy-2,2',2'',2''',2'''',2''''',2'''''',6',6'',6''', 6'''',6''''', 6''''''-trideca-O-methyl-cyclomaltoheptaose).

The characteristics of this compound are as follows:

Thin layer chromatography (Merck Silica Plates) Rf=0.50 in the 9:1 (v/v) $CH_2Cl_2$—MeOH mixture, detection with 10% $H_2SO_4$.

Mass spectrometry: ESI-MS: m/z=1805.95 [M+Na]$^+$ for $C_{86}H_{146}$ $N_2O_{36}Na$.

NMR $^1$H (500 MHz, 25° C., 7 mM solution in $CDCl_3$): attribution by COSY and relay COSY experiments: δ=6.49 (NH CD), 5.70 (NH Chol), 5.38 (H-6 Chol), 5.28–4.88 (H-1, OH-3 CD), 4.11 (H-3 Chol), 3.99–3.16 (H-2, H-3, H-4, H-5, H-6, H-6', $OCH_3$ CD), 2.60–2.48 ($CH_2$ succ, H-4 Chol), 2.04–0.68 (H Chol).

EXAMPLE 2

Preparation of mono-6-(cholest-5-en-3α-ylamide) succinylamide-6-deoxy-2,2',2'',2''',2'''',2''''',2'''''',6',6'', 6''', 6'''',6''''',6''''''-trideca-O-methyl-cyclomaltoheptaose nanoparticles.

The mono-6-(cholest-5-en-3α-ylamide)succinylamide-6-deoxy-2,2',2'',2''',2'''',2''''',2'''''',6',6'',6''', 6'''',6''''',6''''''-trideca-O-methyl-cyclomaltoheptaose nanoparticles are prepared simply by forming an aqueous solution of this cholesteryl-cyclodextrin at a concentration greater than its critical micellar concentration cmc.

The cmc of the cyclodextrin in example 1 was determined with surface tension measurements. The value of the cmc is $9.10^{-6}$ mol/l.

The mean hydrodynamic diameter of the nanoparticles was measured by quasi-elastic light diffusion. The mean diameter MD value calculated according to the Stokes-Einstein approximation based on the interaction-free perfect sphere model is 0.6 nm (60 Å). The static light diffusion analysis of aqueous solutions of nanoparticles at different concentrations ($2.5.10^{-3}$, $5.10^{-3}$ and $10^{-2}$ mol/l) gives a mean aggregate mass of 43,000 g/mol, which is equivalent to a mean of 24 monomers per nanoparticle.

The perfectly spherical shape and the size of the nanoparticles were confirmed by neutron diffusion. The diffusion spectrum obtained from a $10^{-2}$ mol/l solution in $D_2O$ of the cyclodextrin derivative in example 1 is represented in FIG. 1 (spectrum 1).

In FIG. 1, the theoretical spectra simulating spheres (spectrum 2), cylinders (spectrum 3) or lamellae (spectrum 4) formed from the cyclodextrin derivative in example 1, at a concentration of $10^{-2}$ mol/l in $D_2O$, are also shown. Superimposing spectrum 2 simulating spheres with experimental spectrum 1 proves the spherical shape of the cholesteryl-cyclodextrin aggregates. These aggregates are lined on the surface with cyclodextrin cavities available for the inclusion of hydrophobic active molecules, the core being composed of cholesterol groups. The theoretical spectrum simulating spheres gives a mean diameter of 0.5 nm (50 Å) and a mean number of monomers per nanoparticle of 24.

EXAMPLE 3

Preparation of combined mono-6-(cholest-5-en-3α-ylamide)succinylamide-6-deoxy-2,2',2'',2''',2'''',2''''', 2'''''',6',6'',6''',6'''',6''''',6''''''-trideca-O-methyl-cyclomaltoheptaose and Di-Myristoyl-Phosphatidyl-Choline DMPC systems.

An aqueous $15.10^{-3}$ mol/l DMPC solution is prepared either in the form of multilamellar large vesicles MLVs, or in the form of small unilamellar vesicles SUVs, by following the preparation protocols described for example in "Liposomes: a practical approach", R.R.C. New Ed., IRL Press, Oxford University Press, 1990 [11]. To the DMPC MLV or SUV suspension, the cyclodextrin in example 1 is added such that the final cyclodextrin concentration in the aqueous cyclodextrin/DMPC mixture is $0.5.10^{-3}$ or $2.5.10^{-3}$ mol/l.

Figure 2:
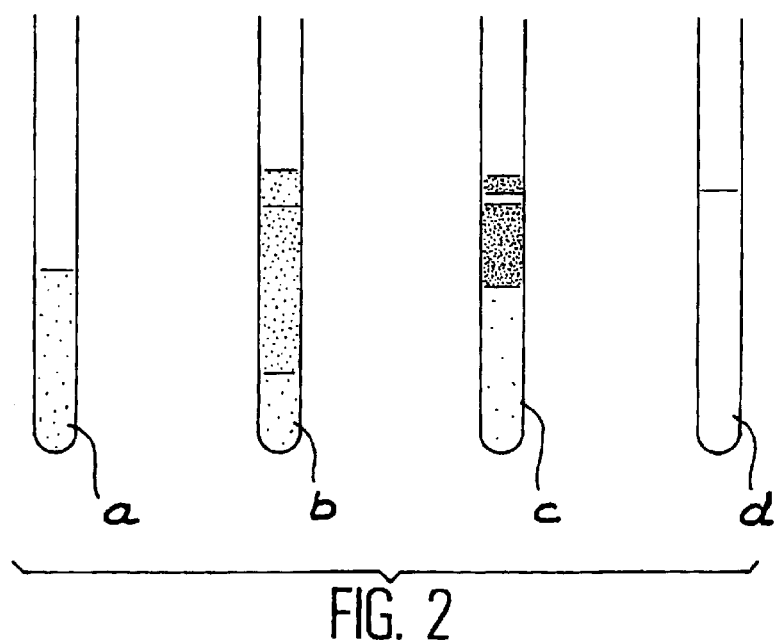
FIG. 2 illustrates the appearance of different cyclodextrin and phospholipid mixtures.

FIG. 2 illustrates the appearance of the different mixtures after 12 hours at 25° C. Tube a contains an aqueous suspension of 15 mM DMPC unilamellar vesicles. Tubes c and d correspond to the following DMPC/cyclodextrin mixtures: $15.10^{-3}/0.5.10^{-3}$ and $15.10^{-3}/2.5.10^{-3}$ mol/l respectively. Tube b is a "control" tube corresponding to the $15.10^{-3}/2.5.10^{-3}$ mol/l DMPC/heptakis(2,6-di-O-methyl)cyclomaltoheptaose mixture, i.e. a mixture of DMPC with a cyclodextrin comprising no steroid substituent.

The different mixtures are examined by $^{31}$P NMR spectroscopy at 81 MHz.

Figure 3:
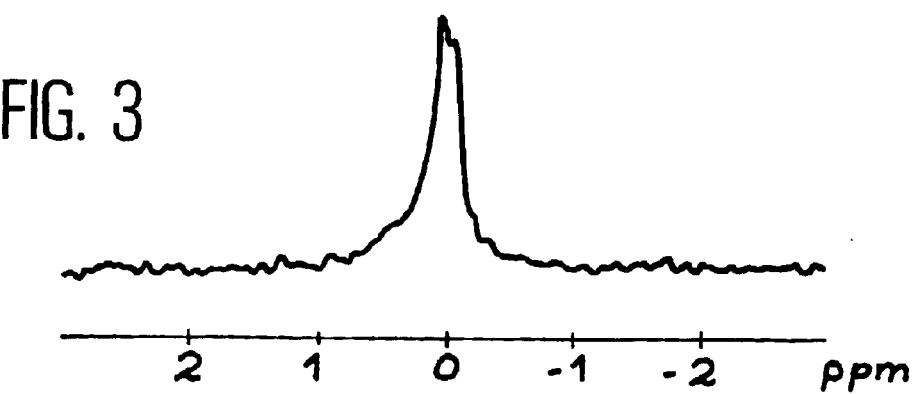
FIGS. 3, 4 and 5 illustrate the $^{31}P$ nuclear magnetic resonance spectra obtained from sample a (FIG. 3), b (FIG. 5) and d (FIG. 4), respectively, in example 3.

FIG. 3 represents the spectrum corresponding to tube a (DPMC only).

Figure 4:
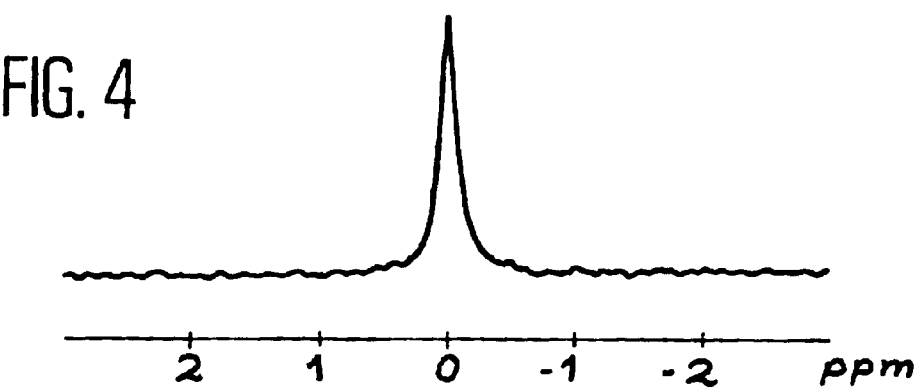

FIG. 4 represents the spectrum corresponding to tube d (DMPC/cyclodextrin mixture; $15.10^{-3}/2.5.10^{-3}$ mol/l).

Figure 5:
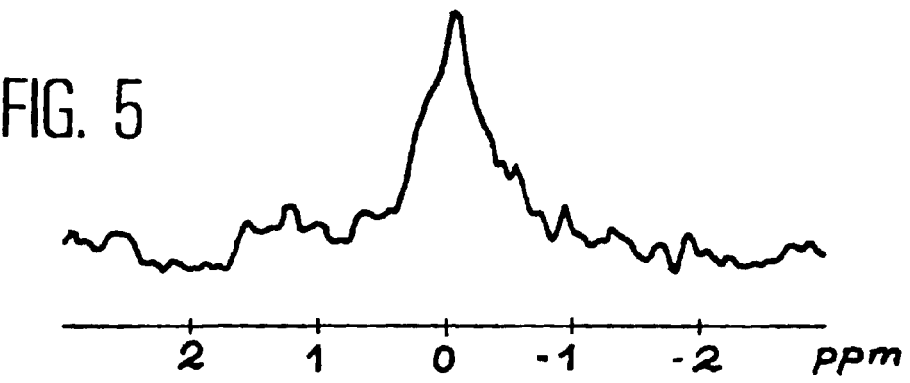

FIG. 5 represents the spectrum corresponding to tube b (DMPC/cyclodextrin mixture according to the prior art).

The existence of small unilamellar DMPC vesicles in tube a is confirmed on the spectrum in FIG. 3 by the presence of two very thin peaks at around 0 ppm corresponding to the phosphors located inside and outside the vesicles.

The spectrum in FIG. 4, which corresponds to sample d, which is perfectly transparent, is reduced to a single thin peak centred at 0 ppm, indicating the presence of smaller aggregates than the unilamellar vesicles in tube a. The spectrum corresponding to the "control" tube b indicates the formation of larger vesicles than the initial vesicles. There is no reorganisation of the medium with this cyclodextrin.

In tube c, the quantity of cyclodextrin according to the invention is too low with reference to the quantity of DMPC to produce a transparent solution as in tube d. A two-phase mixture is obtained.

The mean hydrodynamic diameter of the combined aggregates in sample d was measured by quasi-elastic light diffusion. The mean diameter MD value calculated according to the Stokes-Einstein approximation based on the interaction-free perfect sphere model is 13 nm (130 Å).

Sample d was then examined by neutron diffusion.

Figure 6:
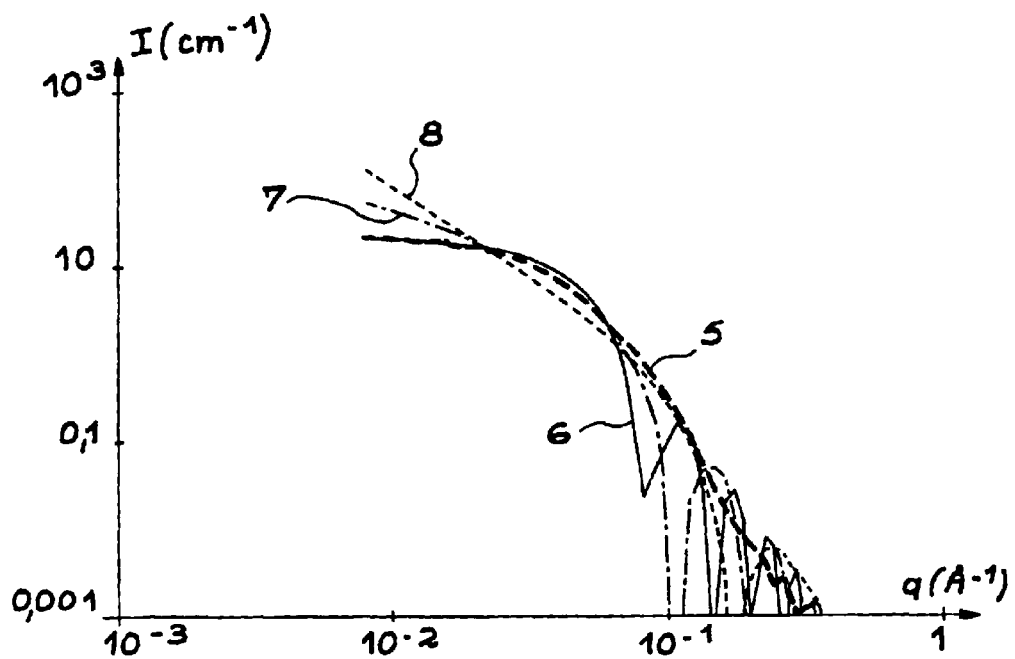
FIG. 6 illustrates the experimental neutron diffusion spectrum, on a logarithmic scale, of a DMPC/cyclodextrin derivative mixture (sample d) obtained in example 3 with three theoretical curves of spherical micellae, cylindrical micellae and double layers.

FIG. 6 illustrates the diffusion spectrum obtained (spectrum 5). In FIG. 6, the theoretical spectra simulating spheres (spectrum 6), cylinders (spectrum 7) or lamellae (spectrum 8) formed from the cyclodextrin derivative in example 1, at a ratio of $15.10^{-3}/2.5.10^{-3}$ mol/l in $D_2O$, are also shown. Superimposing spectrum 6 simulating spheres with experimental spectrum 5 proves the spherical shape of the combined aggregates of DMPC/cyclodextrin according to example 1. These combined spherical systems comprise on their surface cyclodextrin cavities available for the inclusion of hydrophobic active molecules. The theoretical spectrum simulating spheres gives a mean diameter of 10.8 nm (108 Å).

EXAMPLE 4

Preparation of inclusion complexes of the mono-6-(cholest-5-en-3α-ylamide)succinylamide-6-deoxy-2, 2',2'',2''',2'''',2''''',2'''''',6',6'',6''', 6'''',6''''',6''''''-trideca-O-methyl-cyclomaltoheptaose compound with various hydrophobic active molecules.

To an aqueous solution of mono-6-(cholest-5-en-3α-ylamide)succinylamide-6-deoxy-2,2',2'',2''',2'''',2''''',2'''''',6', 6'',6''', 6'''',6''''',6''''''-trideca-O-methyl-cyclomaltoheptaose nanoparticles obtained as in example 2, the hydrophobic compound is simply added either directly, or in solution in a suitable organic solvent, for example acetone, which is allowed to evaporate slowly in air.

Various hydrophobic active molecules were tested and proved to be capable of forming inclusion complexes with the cyclodextrin in example 1. In this way, 16-iodo-3-methylhexadecanoic acid, a fatty acid used as a contrast agent for medical imaging, which had already been solubilised in cyclodextrins, as described in FR-A-2 726 765 [12], was solubilised in an aqueous medium by forming an inclusion complex.

Figure 7:
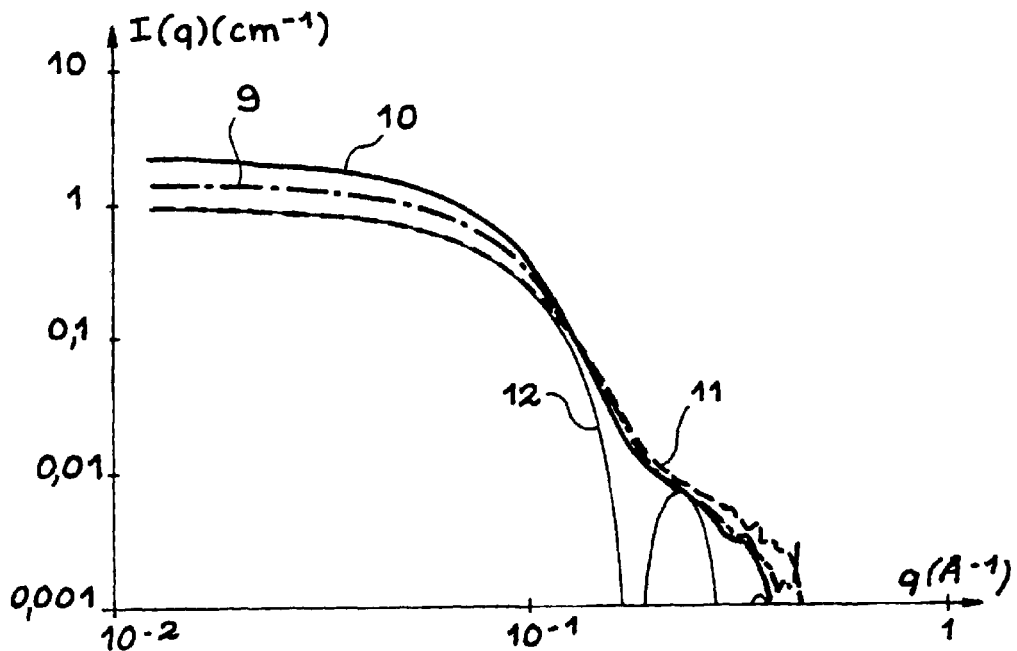
FIG. 7 illustrates the experimental neutron diffusion spectrum, on a logarithmic scale, of mixtures of 16-iodo-3-methylhexadecanoic acid and the cyclodextrin derivative in example 1 (1/1 and 0.1/1 mol) and the neutron diffusion, spectrum of the cyclodextrin derivative in example 1 alone with the theoretical diffusion curve of nanoparticles alone.

FIG. 7 represents the neutron diffusion spectra obtained with:
the solution of nanoparticles of cyclodextrin according to example 1 and the fatty acid (1:0.5 eq. mol) (spectrum 9);
the solution of nanoparticles of cyclodextrin according to example 1 and the fatty acid (1:1 eg. mol) (spectrum 10); and
the solution of nanoparticles of cyclodextrin alone (spectrum 11).

In this figure, the theoretical spectrum (spectrum 12) simulating spheres has also been represented.

In this figure, it can be seen that the incorporation of fatty acid molecules in the nanoparticles of the cyclodextrin according to example 1 results in marked modifications on the diffusion spectra. The intensity I(q) is increased. The Intensity I(q) is proportional to the volume of nanoparticles. The presence of additional molecules (fatty acid molecules) in the nanoparticles increases the value of the contrast and therefore the intensity.

The incorporation in mono-6-(cholest-5-en-3α-ylamide) succinylamide-6-deoxy-2,2',2'',2''',2'''',2''''',2'''''',6',6'',6''', 6'''',6''''',6''''''-trideca-O-methyl-cyclomaltoheptaose nanoparticles of the following hydrophobic compounds:
dothiepin (neurotrope),
chloramphenicol (bacteriostatic),
vitamin A, and
esculin (vascular wall tonic),
were also detected by neutron diffusion.

References

[1]: D. Duchene "Pharmaceutical Applications of Cyclodextrins", published in "Cyclodextrins and their industrial uses", Editions de Santé, Paris 1987, pp. 213–257.

[2]: A. Yabe et al, Thin Solid Films, (1988), 160, pp. 33–41.

[3]: L. Julien et al, "J. Chem. Soc. Perkin Trans 2", 1993, pp. 1011–1022.

[4]: A. Gulik et al in Langmuir (1998), 14, pp. 1050–1057.

[5]: FR-A-2 736 056.

[6]: J. Chem. Soc. Perkin Trans 2, (1998), pp. 2638–2646.

[7]: Uekama and Irie in Chemical Review (1998), 98, pp. 2045–2076.

[8]: Tetrahedron Lett. (1993), 34, pp. 2457–2460.

[9]: J. Chem. Soc. Perkin Trans 2 (1995), pp. 723–730.

[10]: Tetrahedron Lett. (1977), pp. 1977–1980.

[11]: "Liposomes: a practical approach", R.R.C. New Ed., IRL Press, Oxford University Press, 1990.

[12]: FR-A-2 726 765.

What is claimed is:

1. Amphiphilic cyclodextrin derivative complying with the formula:

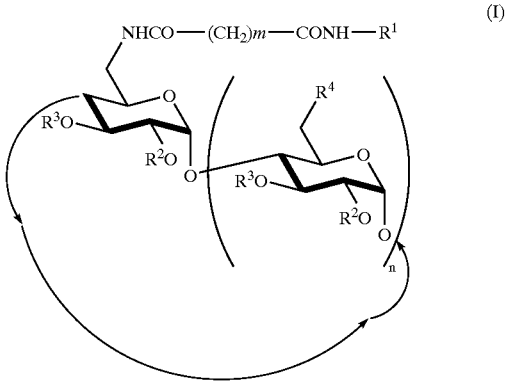

wherein:
$R^1$ represents a steroid,
$R^2$ is selected from the group consisting of an alkyl group, an aryl group, an alkyl group having at least one substitution, and an aryl group having at least one substitution, wherein said substitution is a substituent group selected from the grout) consisting of a halogen atom, a hydroxyl, a carboxyl, and an amine, $R^3$ represents H or $R^2$, all the $R^4$ represent $OR^2$, or one of the $R^4$ represents —NHCO$(CH_2)_m$CONHR$^1$, and the other $R^4$ represent $OR^2$ provided that there is at least one glucose unit where $R^4$ represents $OR^2$ between the two glucose units comprising the substituent —NHCO—$(CH_2)_m$—CONH—$R^1$, m is an integer ranging from 1 to 8, and n is equal to 5, 6 or 7.

2. Cyclodextrin derivative according to claim 1 wherein $R^1$ represents the group according to the formula:

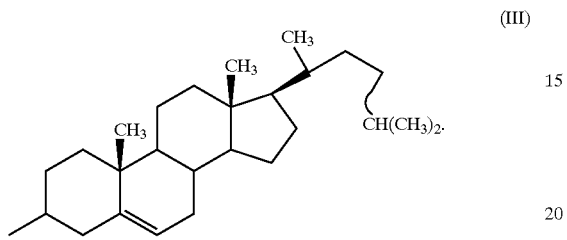

(III)

3. Cyclodextrin derivative according to claim 1, wherein all the $R^4$ represent $OR^2$.

4. Cyclodextrin derivative according to claim 1, wherein $R^2$ represents a methyl group and $R^3$ represents a hydrogen atom.

5. Cyclodextrin derivative according to claim 1, wherein n is equal to 6.

6. Cyclodextrin derivative according to claim 1, wherein m is equal to 2.

7. Cyclodextrin derivative according to claim 2, wherein all the $R^4$ represent $OR^2$.

8. Cyclodextrin derivative according to claim 2, wherein $R^2$ represents a methyl group and $R^3$ represents a hydrogen atom.

9. Cyclodextrin derivative according to claim 2, wherein n is equal to 6.

10. Cyclodextrin derivative according to claim 2, wherein m is equal to 2.

11. Mono-6-(cholest-5-en-3α-ylamide)succinylamide-6-deoxy-2,2',2",2"',2"",2""',2"""',6',6",6"', 6"",6""',6""""-trideca-O-methyl-cyclomaltoheptaose.

12. Method to prepare a cyclodextrin derivative according to the formula:

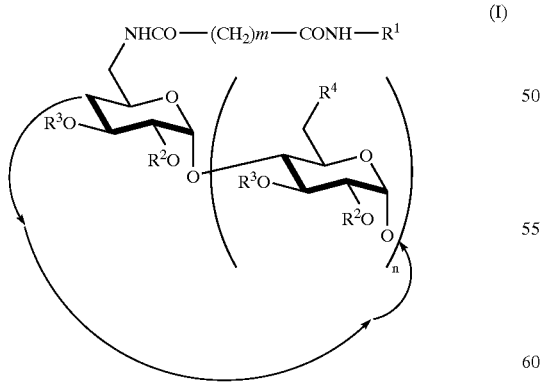

(I)

wherein:

$R^1$ represents a steroid, $R^2$ is selected from the group consisting of an alkyl group, an aryl group, an alkyl group having at least one substitution, and an aryl group having at least one substitution, wherein said substitution is a substituent group selected from the group consisting of a halogen atom, a hydroxyl, a carboxyl, and an amine, $R^3$ represents H, all the $R^4$ represent $OR^2$, or one of the $R^4$ represents —NHCO$(CH_2)_m$CONHR$^1$, and the other $R^4$ represent $OR^2$ provided that there is at least one glucose unit where $R^4$ represents $OR^2$ between the two glucose units comprising the substituent —NHCO—$(CH_2)_m$—CONH—$R^1$, m is an integer ranging from 1 to 8, and n is equal to 5, 6 or 7, which comprises the following steps:

a) react a derivative according to the formula:

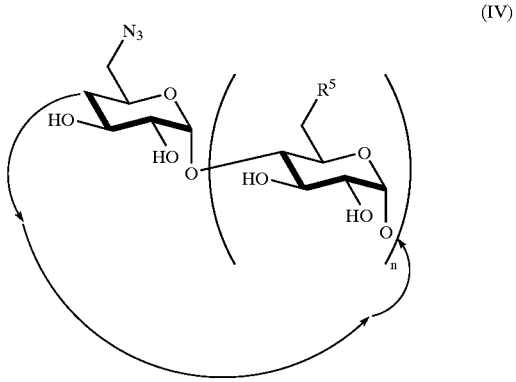

(IV)

wherein all the $R^5$ represent OH, or one of the $R^5$ represents —$N_3$ and the other $R^5$ represent OH, provided that there is at least one glucose unit where $R^5$ represents OH between the two glucose units comprising the $N_3$ substituent, and n is equal to 5, 6 or 7, with a dialkyl sulfate $SO_4R^2{}_2$ where $R^2$ has the significance given above, in a basic medium to obtain the cyclodextrin derivative according to the formula:

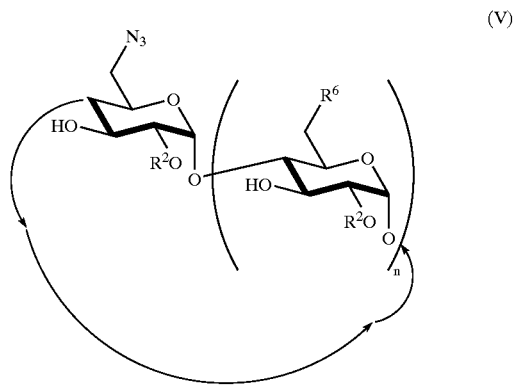

(V)

wherein all the $R^6$ represent $OR^2$, or one of the $R^6$ represents $N_3$ and the other $R^6$ represent $OR^2$, and $R^2$ and n are as defined above, b) perform a Staudinger reaction on the derivative according to formula (V) using triphenylphosphine and ammonia to convert $N_3$ into $NH_2$ and obtain the derivative according to the formula:

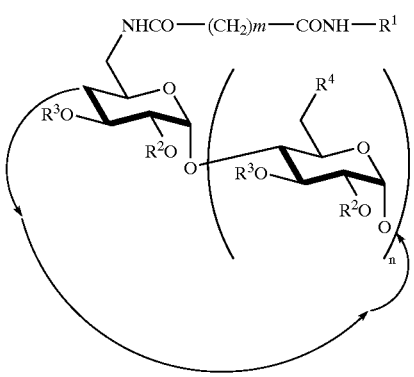

(I)

wherein:
R² is selected from the group consisting of an alkyl group, an aryl group an alkyl group having at least one substitution, and an aryl group having at least one substitution, wherein said substitution is a substituent group selected from the group consisting of a halogen atom, a hydroxyl, a carboxyl, and an amine, R³ represents R², all the R⁴ represent OR², or one of the R⁴ represents —NHCO(CH₂)$_m$CONHR¹, and the other R⁴ represent OR² provided that there is at least one glucose unit where R⁴ represents OR² between the two glucose units comprising the substituent —NHCO—(CH₂)$_m$—CONH—R¹, m is an integer ranging from 1 to 8, and n is equal to 5, 6 or 7, which comprises the following steps:

a) react a derivative according to the formula:

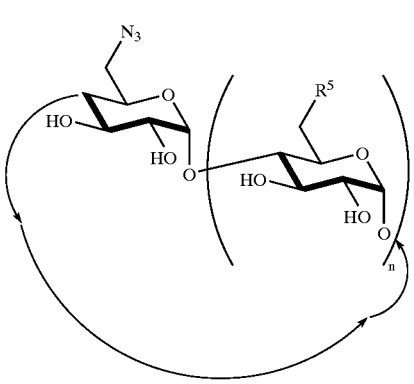

(IV)

wherein all the R⁵ represent OH, or one of the R⁵ represents —N₃ and the other R⁵ represent OH, provided that there is at least one glucose unit where R⁵ represents OH between the two glucose units comprising the N₃ substituent, and n is equal to 5, 6 or 7, with an iodoalkane according to the formula IR² wherein R² has the significance given above, in the

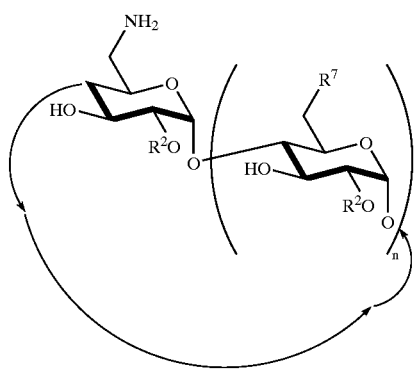

(VI)

wherein all the R⁷ represent OR², or one of the R⁷ represents NH₂ and the other R⁷ represent OR², and R² and n are as defined above, c) react the derivative according to formula (VI) with an acid anhydride according to the formula:

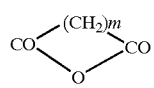

(VII)

where m is as defined above, to obtain the derivative according to the formula:

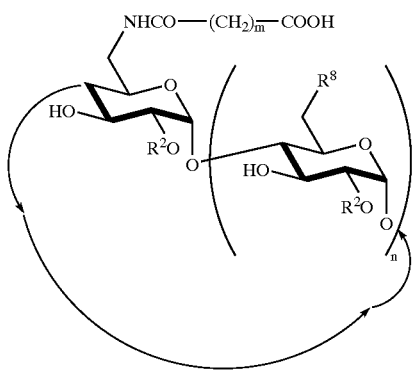

(VIII)

wherein all the R⁸ represent OR², or one of the R⁸ represents —NHCO—(CH₂)$_m$—COOH and the other R⁸ represent OR², and R², m and n are as defined above, and d) react the derivative according to formula (VIII) with a compound according to the formula NH₂—R¹ to obtain the cyclodextrin derivative according to formula (I) defined above.

13. Method to prepare a cyclodextrin derivative according to the following formula:

presence of NaH to obtain the cyclodextrin derivative according to the formula:

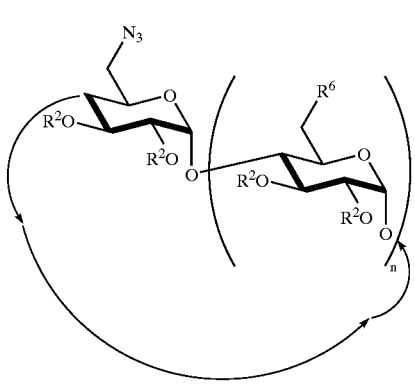

(IX)

wherein all the $R^6$ represent $OR^2$, or one of the $R^6$ represents $N_3$ and the other $R^6$ represent $OR^2$, and $R^2$ and n are as defined above, b) perform a Staudinger reaction on the derivative according to formula (IX) using triphenylphosphine and ammonia to convert $N_3$ into $NH_2$ and obtain the derivative according to the formula:

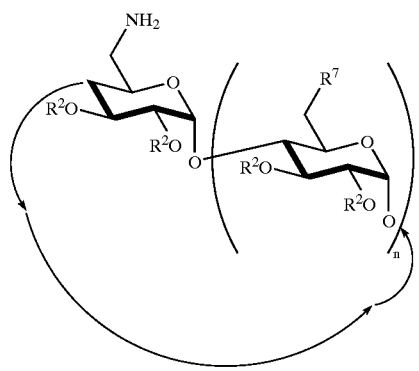

(X)

wherein all the $R^7$ represent $OR^2$, or one of the $R^7$ represents $NH_2$ and the other $R^7$ represent $OR^2$, and $R^2$ and n are as defined above, c) react the derivative according to formula (X) with an acid anhydride according to the formula:

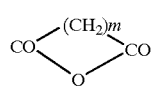

(VII)

where m is as defined above, to obtain the derivative according to the formula:

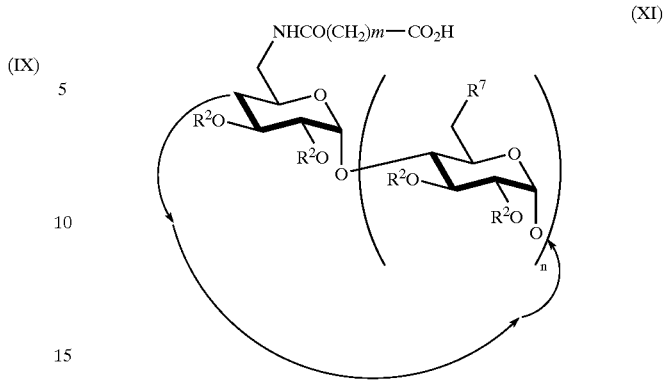

(XI)

wherein all the $R^7$ represent $OR^2$, or one of the $R^7$ represents $-NHCO-(CH_2)_m-COOH$ and the other $R^7$ represent $OR^2$, and $R^2$, m and n are as defined above, and d) react the derivative according to formula (XI) with a compound according to the formula $NH_2-R^1$ to obtain the cyclodextrin derivative according to formula (I) defined above.

14. Inclusion complex comprising mono-6-(cholest-5-en-3α-ylamide)succinylamide-6-deoxy-2,2',2'',2''',2'''',2''''', 2'''''',6', 6''',6'''',6''''',6''''''-trideca-O-methyl-cyclomaltoheptaose and a hydrophobic compound selected from the group consisting of 16-iodo-3-methylhexadecanoic acid, dothiepin, chloramphenicol, vitamin A and esculin.

15. Aqueous solution of solution comprising water and nanoparticles of mono-6-(cholest-5-en-3α-ylamide) succinylamide-6-deoxy-2,2',2'',2''',2'''',2''''',2'''''',6', 6'',6''', 6'''',6''''', 6''''''-trideca-O-methyl-cyclomaltoheptaose or an inclusion complex according to claim 14.

16. Organized surfactant system comprising mono-6-(cholest-5-en-3α-ylamide)succinylamide-6-deoxy-2,2',2'', 2''',2'''',2''''',2'''''',6',6'',6''',6'''',6''''',6''''''-trideca-O-methyl-cyclomaltoheptaose or an inclusion complex according to claim 14 and a surfactant.

17. System according to claim 16 wherein the surfactant is a phospholipid.

18. Aqueous solution comprising (a) water, and (b) a combined system formed from phospholipid or membrane protein vesicles, and mono-6-(cholest-5-en-3α-ylamide) succinylamide-6-deoxy-2,2',2'',2''',2'''',2''''',2'''''',6',6'',6''', 6'''',6''''',6''''''-trideca-O-methyl-cyclomaltoheptaose or an inclusion complex according to claim 14.

* * * * *